April 22, 1952 R. L. BYRUM Plant Pat. 1,083
ROSE PLANT
Filed March 23, 1951
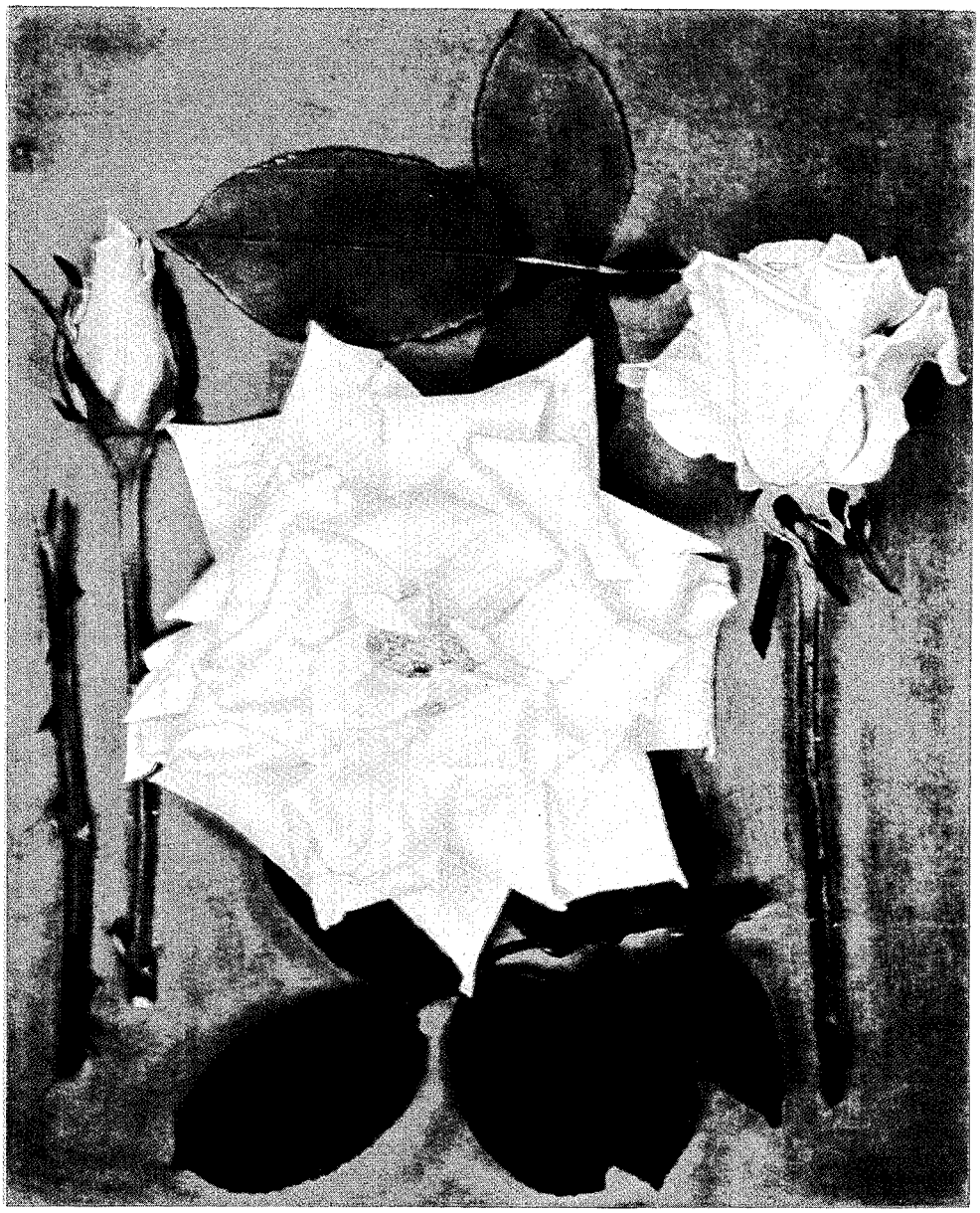
Inventor.
Roy L. Byrum
By: Robert Cobb
Attorneys.

Patented Apr. 22, 1952

Plant Pat. 1,083

UNITED STATES PATENT OFFICE 1,083

ROSE PLANT

Roy L. Byrum, Richmond, Ind., assignor to Joseph H. Hill Company, Richmond, Ind., a corporation of Indiana Application March 23, 1951, Serial No. 217,145

1 Claim. (Cl. 47—61)

The present invention relates to a new and distinct variety of rose plant of the hybrid tea class, originated by crossing the variety "Pearl Harbor" (Plant Patent No. 637) with the unpatented variety "Golden Rapture."

The parent variety "Pearl Harbor" is notable for its vigorous, upright and bushy habits of growth, by its strong and leathery foliage, by its exceptionally great resistance to disease, and by its freedom of bloom and prolific production of well-formed and long-lasting, attractive flowers of camellia-like form.

In this new variety, its foliage, habits of growth and shape of bud and bloom are generally similar to its parent "Pearl Harbor," while its foliage is larger and more dull than the semi-glossy foliage of "Golden Rapture," it is more resistant to blackspot, and it is a heavier and stronger grower than the latter variety.

The parent "Golden Rapture" has a tendency to produce almost white flowers on strong, heavy canes, while the new variety does not do this, and its buds are longer and more pointed than those of this parent. The yellow color of the flowers of the new variety is much more uniform, although somewhat darker towards their center, and the flowers are more nearly alike and hold their color much better during extremely hot weather than those of "Golden Rapture."

The fragrance of the flowers of the new variety is still another outstanding and distinctive characteristic in that it is very delightful and much more pronounced than is the case with "Golden Rapture," particularly when the flowers are displayed in cut-flower groups or masses.

Asexual reproduction of the new variety by budding, by own-rooted cuttings and by grafting at Richmond, Indiana, and elsewhere, shows that the foregoing characteristics come true to form and are established and transmitted through succeeding propagations.

The accompanying drawing shows specimens of the flowers, foliage, stems and thorns of the new variety in different stages of development.

The following is a detailed description of the new variety, with color terminology in accordance with Wilson's Horticultural Colour Chart, except where Koster's Color Guide or Ridgway's Color Standards and Nomenclature are noted, or where general color terms of ordinary dictionary significance are obvious:

Type: Hardy in greenhouse; bush; seedling; for cut-flowers.

Class: Hybrid tea.

Breeding: Seedling.

*Seed parent.*—"Pearl Harbor" (Plant Patent No. 637).

*Pollen parent.*—"Golden Rapture" (unpatented).

Propagation: Holds its distinguishing characteristics through succeeding propagations by cuttings, grafting and budding, which are the only methods tried to date.

Locality where grown: Richmond, Indiana.

*Flower*

Flowers borne: Singly; on strong, long stems.

Quantity of bloom: Free in greenhouse.

Continuity: Continuous.

Fragrance: Moderate; tea.

Bud:

*Peduncle.* — Medium length; medium to heavy; erect; Biscay Green, Plate XVII (Ridgway); entirely smooth; numerous Etruscan Red, Plate XXVII (Ridgway), prickles.

*Before calyx breaks.*—Size—medium. Form—long, pointed with a conspicuous neck; without foliaceous appendages on the surface of the bud; with slender, much-cut foliaceous parts extending beyond the tip of the bud equal to ¾ or more of its length.

*As calyx breaks.*—Color—Lemon Yellow, Plate 4/1, with veins, Plate 4.

*As first petal opens.*—Size—medium. Form—long; pointed. Color—Outside: Lemon Yellow, Plate 4/1—4/2, with veins, Plate 4; inside: Lemon Yellow, Plate 4, at base, shading through Plates 4/1 and 4/2, towards end of petal, with veins, Plate 4.

*Opening:* Opens up well.

Bloom:

*Size, when fully open.*—Medium large; 4 inches to 5 inches.

*Petalage.*—Double; from 25 to 30 petals arranged irregularly.

*Form.*—Open high center at first, becoming open; petals being at first tightly rolled outward; becoming later, at maturity, loosely rolled outward.

Petals: Thick; leathery; with inside satiny and outside shiny.

*Shape.*—Outside—obovate with apex flat. Intermediate—obovate with apex flat. Inside—obovate with apex flat.

This description of a newly opened flower was made from a rose grown in a greenhouse in the month of December 1950, at Richmond, Indiana:

*Color.*—Outside petal—outside surface: Dresden Yellow, Plate 64/1, at base of petal, shading through Plate 64/2 and Plate 64/3 towards end of petal; inside surface: Canary Yellow, Plate 2/1, at base of petal, shading through Plates 2/2 and 2/3 towards end of petal. Intermediate petal—outside surface: Dresden Yellow, Plates 64/1 to 64/2; inside surface: Canary Yellow, Plates 2 to 2/1. Inner petal—outside surface: Dresden Yellow, Plates 64/1 to 64/2; inside surface: Canary Yellow, Plates 2 to 2/1.

This description was made from a rose that was open for three days in a greenhouse in the month of January 1951, at Richmond, Indiana:

*Color.*—Outside petal—outside surface: Canary Yellow, Plate 2/2, at base, shading through Plate 2/3; inside surface: Canary Yellow, Plate 2/2, at base, shading through Plate 2/3. Inside petal—outside surface: Canary Yellow, Plate 2/2, at base, shading through Plate 2/3; inside surface: Canary Yellow, Plate 2/2, at base, shading through Plate 2/3.

*General color effect.*—Newly opened flower—Canary Yellow, Plates 2/1 to 2/2. Three days open—Canary Yellow, Plates 2/2 to 2/3.

*Behavior.*—Persist.

*Flower longevity.*—Cut roses grown in greenhouse kept at living-room temperatures—4 to 5 days.

*Reproductive organs*

Stamens: Medium number; arranged regularly about pistils.

Filaments: Long; few; most with anthers. Color—Barium Yellow, Plate 503.

Anthers: Medium size; all open at once. Color—inside: Barium Yellow, Plate 503; outer edge: Saffron Yellow, Plate 7.

Pollen: Moderate abundance. Color—Orange Cadmium, Plate 10, Koster's Color Guide.

Pilstils: Many.

Styles: Uneven; medium length, thin; bunched.

Stigma: White.

Sepals: Permanent; long; curled. Color—inside: Scheeles Green, Plate 860/3, overlaid with white fuzz; outside: Scheeles Green, Plate 860/3, overlaid with Scheeles Green, Plate 860; some tips Chrysanthemum Crimson, Plate 824/3.

*Plant*

Foliage:

*Leaves.*—Compound of 5 to 7 leaflets; abundant; large; moderately leathery.

*Leaflets.* — Shape — ovoid with apex mucronate. Base—round. Margin—simply serrate.

*Color.*—Mature—upper surface: near Spinach Green, Plate 0960; under surface: near Cedar Green, Plate 80, Koster's Color Guide. Young—upper surface: near Spinach Green, Plate 0960/2, with veins Chrysanthemum Crimson, Plate 824/1, with edges washed lightly with Chrysanthemum Crimson, Plate 824/1; under surface: Sage Green, Plate ooo861/1, shading through Sage Green, Plate ooo861, with veins Chrysanthemum Crimson, Plate 824/1.

*Rachis.* — Medium heavy. Upper side — grooved; hairy; under side—moderately smooth; prickly.

*Stipules.* — Long; medium width; with medium length points turning out at an angle of less than 45°.

*Disease.*—Resistant to mildew and blackspot.

Growth:

*Habit.*—Bush; upright; branched.

*Growth.*—Free; vigorous.

*Canes.*—Heavy.

*Main stems.* — Color — Spinach Green, Plate 0960/1, through Spinach Green, Plate 0960/2. *Thorns*—several; medium length; hooked downward; with short, narrow base. Color — Fawn, Plate 89, Koster's Color Guide. *Prickles* — Few. Color — Fawn, Plate 89, Koster's Color Guide.

*Branches.* — Color — Spinach Green, Plate 0960/1, through Spinach Green, Plate 0960/2. *Thorns* — several; long; hooked downward; with long, narrow base. Color —Fawn, Plate 89, Koster's Color Guide. *Prickles*—few at base. Color—Fawn, Plate 89, Koster's Color Guide.

*New Shoots.* — Color — Oxblood Red, Plate 00823/3. *Thorns* — several; long; hooked downward; with long, narrow base. Color —Oxblood Red, Plate 00823/3. *Prickles*—few at base. Color—Oxblood Red, Plate 00823/3. *Hairs* — Oxblood Red, Plate 00823/3.

I claim:

A new and distinct variety of rose plant of the hybrid tea class, characterized as to novelty by the general similarity of its foliage, habits of growth and shape of bud and bloom to those of its parent "Pearl Harbor" (Plant Patent No. 637), by the uniformity of yellow color of its blooms which shade to a somewhat darker yellow towards their center but hold their color during extremely hot weather, and by the distinctive and pronounced fragrance of its flowers, especially in cut-flower groups, substantially as herein shown and described.

ROY L. BYRUM.

No references cited.